United States Patent
Cornell et al.

(10) Patent No.: US 6,579,434 B1
(45) Date of Patent: Jun. 17, 2003

(54) ELECTRODE WITH REVERSIBLY SEALED FLUORIDE SENSING CRYSTAL

(75) Inventors: Kevin H. Cornell, Rochester, MI (US); Joseph C. Topping, Austin, TX (US); Thaddeus J. Szynal, Farmington Hills, MI (US)

(73) Assignee: Henkel Corporation, Gulph Mills, PA (US)

( * ) Notice: Subject to any disclaimer, the term of this patent is extended or adjusted under 35 U.S.C. 154(b) by 960 days.

(21) Appl. No.: 08/714,914

(22) Filed: Sep. 17, 1996

(51) Int. Cl.⁷ ............................................. G01N 27/333
(52) U.S. Cl. ................................... 204/416; 205/778.5
(58) Field of Search ................................ 204/400, 416, 204/418, 419; 205/778.5, 779, 789

(56) References Cited

U.S. PATENT DOCUMENTS

| | | | |
|---|---|---|---|
| 3,431,182 A | 3/1969 | Frant | ............................. 204/1 |
| 3,830,709 A * | 8/1974 | Krueger et al. | ............. 204/415 |
| 4,049,526 A | 9/1977 | Maurer | ........................ 204/196 |
| 4,128,468 A | 12/1978 | Bukamier | .................... 204/195 |
| 5,393,402 A | 2/1995 | Dervaes et al. | ............. 204/419 |

OTHER PUBLICATIONS

U.S. Ser. No. 08/445,634—Filed May 22, 1995.

* cited by examiner

Primary Examiner—Ta-Hsung Tung
(74) Attorney, Agent, or Firm—Stephen D. Harper; Norvell E. Wisdom (57) ABSTRACT

A free fluoride ion sensitive electrode with longer service life can be obtained by eliminating the use of any cement or similar adhesive to hold the fluoride sensing crystal of the electrode in place within the rest of the structure of the electrode, using instead a pressure sealed combination of the fluoride sensing crystal and upper and lower elastomeric gaskets. This arrangement also permits replacing the crystal and sealing gaskets if needed, without replacing any of the other components of the electrode.

18 Claims, 1 Drawing Sheet

FIG. 1

ELECTRODE WITH REVERSIBLY SEALED FLUORIDE SENSING CRYSTAL

BACKGROUND OF THE INVENTION

1. Field of the Invention

This invention relates to electronic and electrochemical apparatus and methods for measuring the concentration of fluoride ions in aqueous liquid compositions. The general principles of the apparatus are described in U.S. Pat. No. 3,431,182 of Mar. 4, 1969 to Frant, the entire disclosure of which, except to the extend that it may be contrary to any explicit statement herein, is hereby incorporated herein by reference. This invention is more particularly related to modifications that prolong the service life of the electrodes, particularly when the latter are used in contact with hot acidic aqueous compositions containing surfactants and/or oxidizing agents; such compositions are customarily employed in cleaning aluminum beverage containers in a high speed processing line and in forming protective coatings on aluminum surfaces generally. The invention is still more particularly related to an improved method of securing and sealing the fluoride sensing crystal (hereinafter usually abbreviated as "FSC") required for a fluoride sensing electrode within the totality of the electrode, without requiring either (i) the use of cement or other adhesive(s) that undergo a liquid to solid phase transition during the course of construction of the electrode or (ii) molding some other part of the electrode in place around the FSC. Along with its other advantages, this makes the sealing of the FSC reversible, so that if desired the FSC can be replaced without the need for replacing any other component of the electrode.

2. Discussion of Related Art

As already noted briefly above, one of the necessary parts of a fluoride ions concentration sensing apparatus according to both this invention and the prior art is a substantially liquid-impermeable solid body that is constituted of ion-sensitive crystalline fluoride(s), most preferably lanthanum fluoride doped with about 0.3% of europium fluoride. This solid body is usually a single crystal and thus is denoted herein as the "fluoride sensing crystal" or "FSC", even if in some particular instance the solid body might be polycrystalline. In a complete free fluoride ion sensitive electrode, this FSC is physically arranged to have one part of its surface contacted by an ionically conductive liquid in which the concentration of free fluoride ions is to be measured with the aid of the free fluoride ion sensitive electrode. A separate and distinct other area of the FSC surface is in indirect electrical contact, via physical contact with a first liquid ionic solution of known composition, with a first "reference electrode", i.e., an electrode, such as a silver-silver chloride electrode, that automatically maintains itself at a fixed potential as long as the composition of the ionic solution with which it is in contact does not change and the current density flowing through it is small (Because most commercial FSC's are in the form of a relatively thin membrane, it is customary in the art to refer to the two separate and distinct areas of FSC as "[opposite] sides". This terminology may be used in the remainder of this specification, but it is to be understood that despite any use of such terminology, no limitation on the shape of the FSC is thereby intended.) The first ionic solution of known composition, the first reference electrode, and the FSC described above are all assembled within and/or on the surface of a container, usually a tubular container, in such a manner that (i) the FSC has one side in contact with the first ionic solution of known composition and its other side on the outside of the container, (ii) the first liquid ionic solution of known composition is sealed within the container, (iii) the first reference electrode is in physical contact with the first liquid ionic solution of known composition and is not in physical contact with the FSC, but is electrically connected thereto via the first liquid ionic solution of known composition; and (iv) the metallic part of the first reference electrode is connected through a metallic electrical conductor lead to the space outside a sealed space within the container, this sealed space containing all of a metallic part of the first reference electrode, the first liquid ionic solution of known composition, and the interior side of the FSC. The Frant reference teaches that the container may be made of any liquid-impervious, substantially rigid, electrically insulating material that is substantially chemically inert to salt solutions containing fluoride ions with which the container might be placed in contact, and in practice most if not all commercially available free fluoride ion sensitive electrodes have plastic containers, usually of poly(phenylene sulfide), with or without inorganic fillers.

When a free fluoride ion sensitive electrode is in use, the electrical lead from the container for the first reference electrode is connected via a metallic conductor to a low current voltage measuring device and through the latter to a second reference electrode, which may or may not be at the same inherent, self-maintained potential as the first reference electrode. The second reference electrode is in contact with a second liquid ionic solution of known composition, which may or may not be the same as the composition of the first liquid ionic solution, and the second liquid ionic solution is not in substantial physical contact with, but is in indirect electrical contact with, the aqueous composition containing the concentration of free fluoride ions to be measured, the indirect contact being established through one of the devices known in the art, such as a glass fiber, gel or ionic solution, porous TEFLON™ polytetrafluoroethylene plug as described, for example, in U.S. Pat. No. 4,128,468 of Dec. 5, 1978 to Bukamier, "flowing junction", or the like, which permits electrical conductance via ion charge transfer while preventing any substantial physical mixing between the second liquid ionic solution of known composition and the liquid in which the concentration of free fluoride ions is to be measured.

Although fluoride sensitive electrodes of this type have been in use for decades, it has been widely recognized in the art that one of their major disadvantages is an instability of performance. Such instability is usually first manifested as a change in the voltage reading that corresponds to a particular value of free fluoride ions, necessitating frequent recalibration of the particular fluoride sensitive electrode used. Eventually, the electrode may become non-responsive to changes in fluoride concentration within the range in which measurement is needed for the process control of the particular solution being monitored with the electrode, so that the electrode must be replaced. This is a substantial source of expense and also of inconvenience and hazard, inasmuch as many of the solutions in which fluoride concentrations are measured contain hazardous ingredients such as hot hydrofluoric acid, and the free fluoride ion sensitive electrodes are often mounted in the wall of a container vessel for the process solution being monitored, well below the highest liquid level in the vessel; considerable care must be exercised when replacing any component in contact with such a solution in order to avoid injury.

Most prior art attempts to improve the life of free fluoride ion sensitive electrodes have been directed to improving the quality of the seal between the FSC and the container wall in which the FSC is fixed, in order to prevent or at least minimize opportunities for fluid and/or electrical leaks through this desirably completely sealed interface. For example, U.S. Pat. No. 4,049,526 of Sep. 20, 1977 to Maurer teaches that a slow setting type of cement is practically required for sealing the solid fluoride(s) membrane to the insulating container, but that such a slow-setting cement has poor long term resistance to many solutions in which measurement of the free fluoride ion concentration with the free fluoride ion sensitive electrode is desired, so that the slow setting cement, even after it is completely set, should be protected from these solutions with a fast setting cyanoacrylate cement shield.

Most recently than the issue date of the Maurer patent, extensive use has been made of a VITON™ or like fluorocarbon elastomer O-ring or gasket to protect the integrity of the slow setting cement interface between the FSC and the insulating container wall. The FSC normally is cemented into a recess provided in the insulating container wall, so that the bottom surface of the assembly is a flat circular disk that has the FSC as its center, surrounded by an annular ring of cement which itself is surrounded by an annular ring of the material of which the major insulating part(s) of the container wall are constructed. The exterior of the insulating container wall immediately at and away from this flat circular disk is threaded for a sufficient distance to hold in place a retaining collar, with corresponding female threading on its interior cylindrical surface and a circular hole through its flat surface. The sizes of the circular holes in the retaining collar and in the elastomeric O-ring or gasket are at least slightly smaller than the size of the exposed exterior surface of the FSC, and the exterior diameter of the O-ring or gasket is small enough to fit within the retaining collar and large enough to be retained thereby when the latter is screwed into place over the threaded end of the insulating container exterior, so that the O-ring or gasket is compressed and forms a seal that at least initially is liquid tight. However, neither this nor nay other expedient publicly known in the prior art has proved to be fully satisfactory for assuring long term reliability for the free fluoride ion sensitive electrodes now in general use.

U.S. application Ser. No. 08/445,634 filed May 22, 1995, now U.S. Pat. No. 5,565,076, and assigned to the same assignee as this application, the entire specification of which, except for any part thereof that may be inconsistent with any explicit description in this specification, is hereby incorporated herein by reference, teaches an improvement of conventional fluoride sensing electrodes by providing a solid shield member that prevents contact between the fluid in which fluoride ion concentration is to be measured and the outer part of the container for the first reference electrode and the first ionic solution of known composition. This achieves a significant improvement in electrode life, but still normally makes use of a cement or adhesive as part of the means that secure and seal the FSC into the total electrode structure. As a result, if a replacement membrane is needed, other parts of the apparatus must be replaced as well.

DESCRIPTION OF THE INVENTION

Objectives of the Invention

One major objective of the invention is to prolong the time interval between recalibrations and/or replacements of free fluoride ion sensitive electrodes by providing an improved type of free fluoride ion sensitive electrode. compared with those publicly known from prior art. Another alternative or concurrent objective is to provide an electrode in which the FSC is reversibly sealed and secured in place, so that it can be replaced without replacing any other part of the electrode. Another alternative or concurrent objective is to improve the operation of processes utilizing free fluoride ion sensitive electrodes by utilizing electrodes with longer service life. Other objectives will be apparent from the description below.

SUMMARY OF THE INVENTION

It has been discovered that a suitably shaped FSC for a free fluoride ion sensitive electrode can be adequately secured and sealed in place by appropriate purely mechanical means and that these means also achieve an improved life for the electrode in service in at least some adverse environments of practical importance.

Accordingly, one major embodiment of the invention is a free fluoride ion sensitive electrode that comprises, or preferably consists essentially of, the following components:

(A) a substantially liquid-impermeable solid fluoride sensing crystal that is constituted of one or more fluoride ion-sensitive solid, crystalline, substantially water insoluble fluorides, this crystal being usually denoted briefly herein as the "FSC" and having a size and a shape;

(B) first and second solid elastomeric gaskets, each of said gaskets having a size, a shape, a solid exterior surface, and a hole through the gasket, said hole having a size, a shape, a boundary surface including two ends, and a position within the elastomeric gasket such that:

(1) there exists at least one hypothetical infinite, liquid-impermeable plane in three dimensional space in which said gasket can be hypothetically embedded so that, when each point of said hypothetical plane that coincides with a point of the gasket or of the hole therethrough is hypothetically replaced by a point of the gasket or of the hole therethrough with which a point of the hypothetical plane coincides, there results a hypothetical structure for which all of the following properties are true:

(a) one end of the hole is situated entirely on one side of the plane and the other end of the hole is situated entirely on the opposite side of the plane;

(b) there exists a first area of finite size, on the solid exterior surface of the gasket, that is entirely on one side of the plane and that completely surrounds the end of the hole on said one side of the plane and there exists a second area of finite size on the exterior surface of the gasket that is entirely on the side of the plane opposite from said first area of finite size and that completely surrounds the end of the hole on the side of the plane opposite from said first area of finite size; and (c) the hypothetical structure includes no physical impediment to the passage of any liquid from one side of the plane to the other through the hole in the gasket, but does not allow such passage of any liquid from one side of the plane to the other by any route that does not lie wholly within the hole in the gasket;

and (2) there exists at least one relative orientation in space among the FSC and said first and second elastomeric gaskets, said relative orientation in space having all of the following properties:

(a) there exist distinct first, second, and third infinite hypothetical lines jointly having all of the following properties: at least two segments of said first infinite hypothetical line lie entirely within said first elastomeric gasket on opposite side of another segment of the first infinite hypothetical line that does not coincide with any solid part of said first elastomeric gasket; at least two segments of said second infinite hypothetical line lie entirely within said second elastomeric gasket on opposite sides of another segment of the second infinite hypothetical line that does not coincide with any solid part of said second elastomeric gasket; exactly one segment of said third infinite hypothetical line lies entirely within said FSC; said first, second, and third infinite hypothetical lines are parallel to one another and are perpendicular to that direction along which Earth locally exerts its strongest gravitational force, said direction being hereinafter usually denoted as "the vertical direction" or "local vertical";

(b) along the vertical direction, the FSC is between the two elastomeric gaskets, so that one gasket may be conventionally described as "upper" and the other gasket as "lower";

(c) at least one finite volume of any liquid may be maintained within a space bounded on its bottom by the FSC and on its sides by solid portions of the upper elastomeric gasket without any loss in volume of said liquid resulting from gravitationally induced permeation of said liquid between the FSC and the upper elastomeric gasket; and (d) if said relative orientation in space of the FSC and the two elastomeric gaskets is inverted, so that the elastomeric gasket which was formerly the lower gasket becomes the upper gasket, at least one finite volume of any liquid may be maintained within a space bounded on its bottom by the FSC and on its sides by solid portions of the upper elastomeric gasket without any loss in volume resulting from gravitationally induced permeation of said liquid between the FSC and the upper elastomeric gasket, any relative orientation in space among the FSC and the two elastomeric gaskets that possesses all of properties (a)–(d) as recited immediately above, and any other relative orientation in space among these three components that can be moved, without altering any distance between any two points each of which is situated within one of the three components but one of which may be in a different one of the three components from the other, so as to possess all of properties (a)–(d) as recited immediately above, being defined for use hereinafter as a "sealing array" of these three components;

(C) a primary container body constituted of electrically insulating material and having walls surrounding a central cavity that extends completely through the primary container body, thereby forming a first and a second end of said central cavity, said central cavity having a size and a shape such that there exists an orientation of the container body in three dimensional space in which at least one sealing array of the FSC and the two elastomeric gaskets is retained against any force exerted by natural gravitation of Earth within a portion of the walls of the primary container body surrounding the first end of the central cavity, in such a manner that:

(1) a portion of the FSC is in contact with the central cavity of the primary container body; and (2) at least one fixed volume of any liquid may be maintained within a space bounded by the FSC, solid portions of the lower elastomeric gasket, and the walls of the primary container body without any loss in volume resulting from gravitationally induced permeation of said liquid between the FSC and the lower elastomeric gasket or between the walls of the primary container body and either of the lower elastomeric gasket or the FSC, any relative orientation in space among the FSC, the two elastomeric gaskets, and the primary container body that includes a sealing array of the FSC and the two elastomeric gaskets and that satisfies conditions (1) and (2) as recited immediately above, or any other relative orientation in space among these four components that can be moved, without altering any distance between any two specified points each of which is situated within one of the four components but one of which may be in a different one of the four components from the other, so as to produce a relative orientation in space among these four components that includes a sealing array among the FSC and the two elastomeric gaskets and that satisfies conditions (1) and (2) as recited immediately above, being defined for use hereinafter as a "sealing array" among these four components;

(D) means for maintaining a sealing array among the FSC, the two elastomeric gaskets, and the primary container body when they are jointly rotated, i.e., when the positions of the FSC, the two elastomeric gaskets, and the primary container body are all jointly varied with respect to local vertical but without altering any distance between any two distinct points each of which is located within one of these four components but one of which may be in a different one of the four components from the other, said means not including use of any cement or adhesive or any incorporation of the FSC into a cohesive unitary solid from which it can not be removed intact without dividing all parts of the unitary solid that do not consist of the FSC into at least two separate pieces;

(E) means for dividing the central cavity of the primary container body so as to constitute jointly from said means for dividing, the primary container body, the FSC, and at least one of the two elastomeric gaskets boundaries of a liquid- and vapor-tight portion of the central cavity of the primary container body;

(F) a volume of a first liquid ionic solution of known composition and concentration confined within said substantially liquid- and vapor-tight portion of the central cavity of the primary container component (C) and in physical contact with FSC component (A);

(G) a first reference electrode enclosed within said substantially liquid- and vapor-tight portion of the central cavity of the primary container component (C), said first reference electrode including a metallic electrical conductor that is in physical contact with ionic solution component (F) but is not in physical contact with FSC component (A); and (H) an electrically conducting lead component that is in physical contact with both the metallic electrical conductor part of reference electrode component (G) and a point outside said substantially liquid- and vapor-tight portion of the central cavity of the primary container component (C) but is not in physical contact with FSC component (A) or with first ionic solution component (C).

Another major embodiment of the invention is a process comprising steps of (i) monitoring the free fluoride ions concentration of a reactive process liquid as the process liquid is used by measuring the voltage developed between a free fluoride ion sensitive electrode and a second reference electrode when both of these electrodes are in electrical contact with the process liquid and (ii) adjusting the free fluoride ions concentration of the process liquid when necessary to maintain said concentration between preselected limits, wherein an electrode according to the invention as described above is used as the free fluoride ion sensitive electrode.

DETAILED DESCRIPTION OF THE INVENTION, INCLUDING PREFERRED EMBODIMENTS

Figure 1:
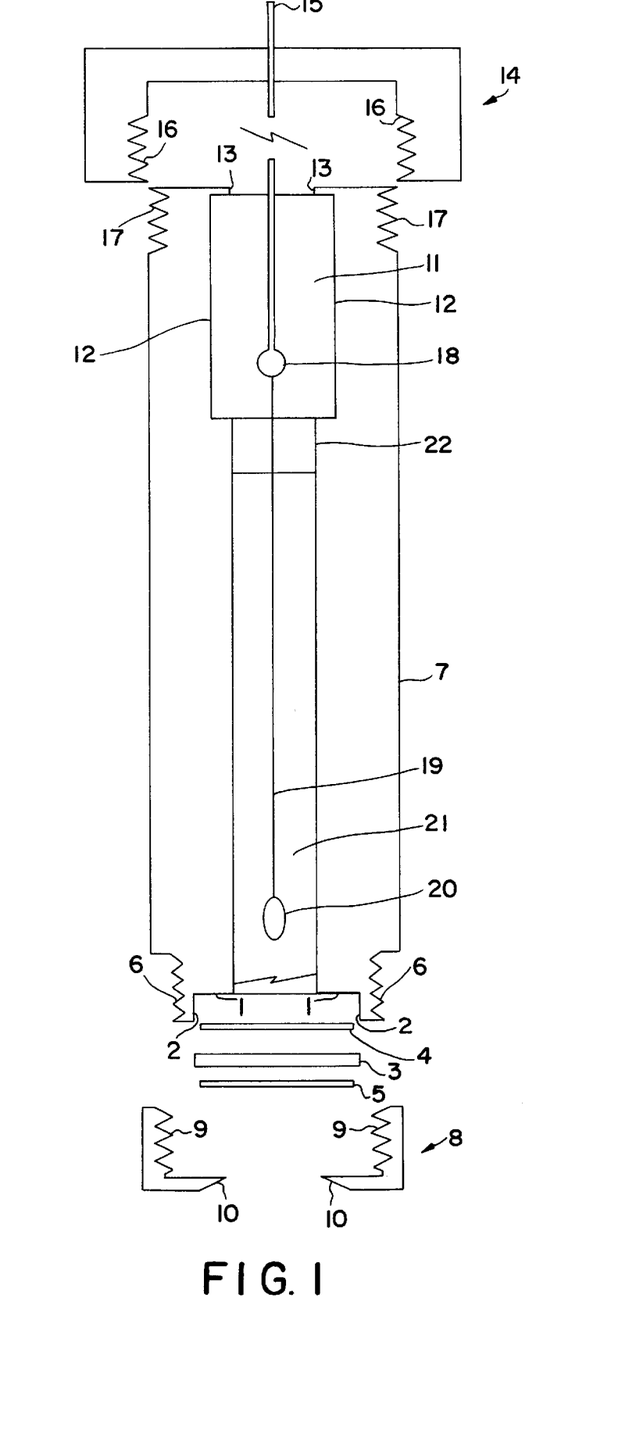
FIG. 1, the sole drawing FIGURE, is an exploded sectional view of a preferred embodiment of a fluoride sensing electrode according to the invention.

The primary container body is generally most conveniently made in a generally elongated right circular cylindrical shape (the term "cylinder" and all its grammatical variations hereinafter being understood, unless explicitly stated to the contrary, (i) to mean "right circular cylinder" and its corresponding grammatical variations and (ii) to include screw threaded as well as simple cylindrical surfaces), with the central cavity having the general form of another cylinder that is concentric with the cylinder defining the outer surface of the primary container body. The generalized cylindrical shapes of both the primary body itself and of its central cavity preferably deviate from those of simple cylinders in their end portions in a manner described below with reference to the sole drawing figure.

The first end portion of the central cavity of the primary container body preferably has the shape of a cylinder that is concentric with but has a larger diameter than the cylindrical central portion of the central cavity, so that the inner wall surface of the primary container body in this first end portion consists of two concentric cylinders joined by an annular disk with a circular center hole, the disk and center hole both being concentric with the two concentric cylinders. The solid portion 1 of this annular disc and the end portion 2 of the walls of the primary container body surrounding the central cavity then bound a space in which an array of an FSC 3 and two elastomeric gaskets 4 and 5 can be retained in a mutually sealing configuration as described above. When the first end portion of the central cavity of the primary container has this preferred shape, the FSC is preferably a solid cylinder and each of the elastomeric gaskets preferably is a cylinder with a cylindrical hole therethrough or is a torus.

When the primary container body has this preferred shape, the most preferred means for maintaining a sealing relative orientation among the FSC, the two elastomeric gaskets, and the primary container body comprises the following components:

(A') male screw threads 6 on an exterior first end portion of the walls 7 of the primary container body; and
(B') a first end cap component 8 comprising:
 (1) a primary cylinder having a concentric cylindrical hole therethrough, so that the primary cylinder has exterior and interior walls and distinct first and second ends of each of the exterior and interior walls;
 (2) a retainer portion 10 joined to the primary cylinder portion at its second end; and
 (3) a continuous zone of female screw threads 9 on at least a part of the interior wall of the primary cylinder portion, said female screw threads being matable with the male screw threads on the exterior first end portion of the walls of the primary container body when these male screw threads are inserted into the first end of the interior walls of the first end cap component, said retainer portion and said primary cylinder portion together forming a liquid-tight container for a sealing array among said fluoride-sensing crystal and said first and second elastomeric gaskets, i.e., said retainer portion having a size, a shape, and a hole therethrough having a size and a shape and said primary cylinder having a size and an orientation relative to the retainer portion, such that, (i) when the first end cap component is arranged in space with the vertical direction coinciding with the axis of the primary cylinder portion of the first end cap and the second end of said primary cylinder portion is below its first end; at least one sealing array of the FSC and the two elastomeric gaskets fits within the first end cap component and is retained thereby against local Earth gravity to form a contained sealing array of the FSC and the two elastomeric gaskets, and (ii) there exists at least one depth value such that, if the first end cap component containing said contained sealing array of the FSC and the two elastomeric gaskets is immersed in any chemically non-reactive liquid to said depth value, while maintaining the axis of the primary cylinder portion of the first end cap coincident with local vertical and the second end of the primary cylinder portion of the first end cap below the first end thereof and maintaining said sealing array of the FSC and the two elastomeric gaskets, said liquid in which the contained array is immersed does not cover the first end of the primary cylinder portion of the first end cap but is nevertheless in contact with the FSC, said male screw threads on the primary container body, first end cap component, primary cylinder portion of the first end cap component, concentric cylindrical hole therethrough, exterior and interior wall portions of the first end cap component, zone of female screw threads on at least part of said interior walls of the primary cylinder, retainer portion of the first end cap component, and hole therethrough all forming a torque-limited-screwed, temperature-stable sealed container around the sealing array among the fluoride-sensing crystal and the first and second elastomeric gaskets, i.e., said male screw threads on the primary container body, first end cap component, primary cylinder portion of the first end cap component, concentric cylindrical hole therethrough, exterior and interior walls of the first end cap component, zone of female screw threads on at least part of said interior walls of the primary cylinder, retainer portion of the first end cap component, and hole therethrough all having sizes, shapes, and spatial orientations relative to one another and being constituted of materials with elastic moduli such that there exist a torque limit value and a specific relative spatial orientation among the FSC, the two elastomeric gaskets, and the first end portion of the primary container body that retains the FSC and the two elastomeric gaskets all jointly having the property that, when the FSC and the two elastomeric gaskets are retained within said first end portion of the primary container body and said female screw threads on the interior walls of the first end cap component are mated with said male screw threads on the first end of the primary container body to the maximum extent possible, without exerting on either the first end cap component or the primary container body a torque greater than said torque limit value, while all of the FSC, the two elastomeric gaskets, the first end portion of the primary container body that retains the FSC, and the two elastomeric gaskets are at a single assembly temperature, an assembly of the primary container body, the FSC, the two elastomeric gaskets, and the first end cap component is formed and includes a sealing array among the FSC, the two elastomeric gaskets, and the primary container body that (i) is maintained without requiring any imposition of mechanical force from any external source, so long as none of the previously mated threads of the primary container body and the first end cap are unmated and (ii) is not separated or otherwise damaged by any gas pressure or thermal expansion mismatch generated when the temperature of the entire free fluoride ion sensing electrode or any part of it is varied not more than 50° C. from the assembly temperature.

In the drawing figure, the zone of female screw threads on the interior wall of the primary cylinder of the first end cap extends completely to the first end of the first end cap. This is normally the most convenient design, but is not required. The only necessity is that any part of the first end cap component between its first end and the beginning of the zone of screw threads must be sufficiently large to accommodate the make threaded first end of the primary container body. For example, if desired, the end cap component can be extended in length so as to provide a complete shield for the electrode as described in detail in U.S. application Ser. No. 08/445,634 already cited above. Also, a shield body as described in that Application, which need not have screw threads at all although it usually does, can be used instead of an end cap as described above to maintain a sealing array of the FSC and the two elastomeric gaskets in an electrode according to this invention.

The means for dividing the central cavity of the primary container body are preferably constituted of a plug 11 of solidified potting resin such as epoxy resin or the like. In order to secure this plug more reliably in place, there preferably is an enlarged zone 12 of the central cavity through the primary container body, both ends of said enlarged zone of the central cavity being within, rather than at either end of, the primary container body and both of the ends of the enlarged zone being between the second end of the primary container body and the liquid- and vapor-tight portion of the central cavity of the primary container body that contains the first ionic solution of known composition, said enlarged zone being larger in cross-section than another portion 13 of said central cavity that is situated between the enlarged zone and the extreme second end of said central cavity, in order to generate a mechanical interlock between the primary container body and the potting resin, at least a portion of which fits within the enlarged zone and has a larger cross-section than the extreme second end portion of the central cavity. If the central cavity of the primary container body has the preferred cylindrical shape, the enlarged zone is preferably a concentric cylinder of slightly larger diameter. Unless it is known that this second end of the primary container body of the electrode will never be exposed in use to any environment that might promote degradation of the potting resin, the second end is preferably closed by a second end cap 14, substantially the same in general design as the first end cap, except that (i) the hole through the central disk of its closed end preferably is as close as is reasonably possible in size and shape to the size and shape of the electrical lead component 15 that passes through it and (ii) the second end cap may be of any convenient length, because it does not need to accommodate the FSC or other object(s) of substantial thickness within its interior. Preferably, a zone near the more widely open end of the second end cap is provided with female screw threads 16 that mate with a zone of male screw threads 17 provided on the second end of the primary container body.

Other elements shown in the drawing figure, which are not particular to this invention but are necessary or optional parts of a complete fluoride sensing electrode, are an externally electrically insulated but internally electrically conducting connector 18 between insulated electrical lead 15 and a bare silver wire 19 that is connected on its other end to a pellet 20 of silver chloride. The silver wire, silver chloride pellet, and a volume of ionic aqueous solution of known composition 21 constitute the first reference electrode described above. Element 22 is a temporary plug used in forming plug 11 from liquid potting resin during one method of construction of the electrode that has been found satisfactory.

In this method of construction, lead 15, connector 18, and silver wire 19 with silver chloride pellet 20 attached are inserted within a pre-machined primary container body and held in place by temporary plug 22, which is most often made of tightly packed surgical cotton or some similar material that is chemically inert to potting resin and to the first electrolyte solution of known composition. (External clamps may also be used if desired to hold these elements in place.) Then potting resin in liquid form is introduced into the space above temporary plug 22 in an amount sufficient to fill the enlarged zone of the primary container body, which has been provided to accommodate it, after the potting resin has solidified. After this solid resin plug 11 is in place, the primary container body is inverted from its previous position and filled from its first end with the first ionic solution of known composition 21. Elastomeric gaskets 4 and 5 and FSC 3 are then emplaced between end portions 2 of the walls of the primary container body so that gasket 4 is against solid portion 1 of the annular disk joining the smaller cylindrical walls defining the space in which the first ionic solution is accommodated and the larger cylindrical walls of the primary container body in end portions 2, and first end cap 8 is screwed into place, with use of a torque wrench, so that threads 9 mate with threads 6 to generate a sealing array among the primary container body, the two gaskets, and the FSC. Second end cap 14 liquid-tight seal may be screwed into place at any time after the potting resin has solidified to form plug 11.

Each of the primary container body and the first and second end caps when used ordinarily is preferably a single continuous body, but can also be assembled from two or more pieces by any means conventional in the assembly arts without departing from the spirit of the invention, unless something about the assembly process or the resulting assembly frustrates one of the objectives of the invention. Each of these components may be constructed from a wide variety of materials. Because an electrode according to the invention is normally assembled at a temperature conducive to human comfort and is normally used at a much higher temperature, the material(s) of construction for these components preferably have coefficients of thermal expansion (hereinafter usually abbreviated as "CTE") that are not too far different from those of the FSC—all suitable materials known for constituting the FSC have rather anisotropic thermal expansion properties, which must be accommodated by the other components of the electrode. More particularly, the CTE of the material from which the primary container and, if used, the end caps are constructed preferably is at least, with increasing preference in the order given, 0.5, 1.0, 2.0, 3.0, 4.0, 5.0, 6.0, 7.0, 8.0, 9.0, or $9.8\times10^{-5}$ per ° C. and independently preferably is not more than, with increasing preference in the order given, 100, 75, 50, 40, 35, 30, 25, 20, 17, 14, 12, or $10\times10^{-5}$ per ° C.

Independently, the material(s) of which the primary container and, if used, the end caps are constructed preferably is not too rigid, so that it can contribute to the sealing properties of the interfaces between it and other bodies. This material must, of course, be rigid enough to hold the array of FSC and two elastomeric gaskets in place in preferred embodiments of the invention as described above. More particularly, independently for each modulus stated, material(s) of which the primary container and, if used, the end caps are constructed preferably have: a modulus of elasticity in compression that is at least, with increasing preference in the order given, 0.4, 0.8, 1.2, 1.6, 2.0, 2.4, 2.8, 3.2, 3.6, 4.0, 4.2, 4.4, 4.6, or $4.8\times10^7$ kilograms per square meter (hereinafter usually abbreviated as "$kg/m^2$") and independently preferably is not more than, with increasing preference in the order given, 50, 40, 30, 20, 16, 12, 10, 9.0, 8.0, 7.5, 7.0, 6.6, or $6.4\times10^7$ $kg/m^2$; a modulus of elasticity in tension that is at least, with increasing preference in the order given, 0.2, 0.4, 0.6, 0.8, 1.0, 1.2, 1.4, 1.6, 1.8, 2.0, 2.2, 2.4, or $2.6\times10^7$ $kg/m^2$ and independently preferably is not more than, with increasing preference in the order given, 40, 30, 20, 16, 12, 10, 9.0, 8.0, 7.0, 6.0, 5.5, 5.0, or $4.5\times10^7$ $kg/m^2$; and a modulus of elasticity in flexure that is at least, with increasing preference in the order given, 0.4, 0.8, 1.2, 1.6, 2.0, 2.4, 2.8, 3.0, 3.2, 3.4, 3.6, 3.8, or $4.0\times10^7$ $kg/m^2$ and independently preferably is not more than, with increasing preference in the order given, 40, 30, 20, 16, 12, 10, 9.0, 8.0, 7.0, 6.0, 5.5, 5.0, or $4.5\times10^7$ $kg/m^2$. (The moduli in compression and tension are measured according to American Society for Testing and Materials, hereinafter usually abbreviated as "ASTM", Method D638 and the modulus in flexure is measured according to ASTM Method D747.)

As briefly mentioned above, one reason for preferring materials of construction for the primary container that are not excessively rigid is that this makes possible the formation of an additional sealing contact between the FSC and the primary container wall when these components have suitable shapes and sizes and the gasket sizes are properly adjusted. In a particularly preferred embodiment, when all of the FSC, the elastomeric gaskets, and the first end of the primary container have their preferred cylindrical shapes as already described above, the FSC preferably has an outside diameter that is at least, with increasing preference in the order given, 90, 94, 95, 96, 97, 98, 99.0, 99.2, 99.4, 99.6, or 99.8% of the inside diameter of the inner wall surface of the primary container body in said first end portion. Independently, each elastomeric gasket preferably has an outside diameter that is not greater than, with increasing preference in the order given, 99, 98, 97, 96, 95, 94, 93, 92, 91, or 90% of the outside diameter of the FSC. When the diameter of the FSC is sufficiently close to that of the walls of the first end of the primary container body that retain the FSC and these walls have at least moderate flexibility as defined above, it is believed that an additional sealing contact is formed between the outer cylindrical surface of the FSC and the walls of the primary container. Also, moderate flexibility promotes the formation of screwed joints that retain their sealing properties over a long time and that are not easily damaged by internal or external pressures to which the electrode may be subjected—the electrodes are normally assembled at a temperature near 25° C. and used at a substantially higher temperature, so that outgassing from the first liquid ionic solution can create substantial internal pressure, and the electrodes can be, although they usually are not, used in pressurized vessels and in such use could be subjected to substantial external hydraulic pressure.

Chemically, the preferred materials of construction for the primary container body and, if used, the end caps are plastics, more preferably fluorocarbons, or most preferably poly(tetrafluoroethylene), which also has mechanical properties within the preferred ranges specified above and is sufficiently hydrophobic to resist penetration by aqueous solutions into any narrow passageways that may exist between two adjacent elements of this material, as a result of thermal expansion mismatches and/or small imperfections in machining the elements into shapes that will fit closely with each other.

The elastomeric gaskets most preferably are made of a copolymer of tetrafluoroethylene and perfluoro (methylvinylether), commercially available under the trade name KALREZ. Next most preferred are other commercially available fluorocarbon elastomers such as (i) copolymers of vinylidene fluoride and hexafluoropropylene and terpolymers of vinylidene fluoride, tetrafluoroethylene, and hexafluoropropylene, both available under the trademarks DAI-EL, FLUOREL, TECHNOFLON, and VITON from Diakin, 3M, Montedison, and DuPont respectively and (ii) copolymers of vinylidene fluoride and chlorotrifluoroethylene, available under the trademark KEL-F from 3M. If only relatively chemically benign liquids are to be tested for free fluoride ions concentrations with a free fluoride ion sensitive electrode according to the invention, less expensive elastomers than these may be equally suitable.

In order to accommodate the mechanical stresses involved in forming such a sealing contact between the FSC and the container wall, it has been found that a cylindrical FSC used in a highly preferred embodiment according to the invention preferably has a larger length (i.e., distance from one circular surface of the cylinder to the other circular surface of the cylinder along the axis of the cylinder) to diameter ratio than has been common for FSC's used in prior art types of fluoride sensing electrodes. More particularly, an FSC used in the most highly preferred embodiment of this invention has a length to diameter ratio that is at least, with increasing preference in the order given, 0.25, 0.30, 0.35, 0.40, 0.45, or 0.50.

In many cases, free fluoride ion sensitive electrodes are now utilized in a liquid tight mounting or housing, with a fluoride sensing crystal and most or all of the other parts of the free fluoride ion sensitive electrode located well below the highest level of liquid in which the fluoride ions concentration is to be measured with the free fluoride ion sensitive electrode. Electrodes according to this invention are well suited to use in this manner.

What is claimed is:

1. A free-fluoride-ion-sensitive electrode comprising:
(A) a substantially liquid-impermeable solid fluoride-sensing crystal that is constituted of one or more fluoride-ion-sensitive solid, crystalline, substantially water-insoluble fluorides;
(B) first and second solid elastomeric gaskets that form a sealing array with the fluoride-sensing crystal;
(C) a primary container body constituted of electrically insulating material and having walls surrounding a central cavity that extends completely through the primary container body, thereby forming a first and second end of said central cavity, said central cavity having a size and a shape such that a sealing array among the primary container body, the fluoride-sensing crystal, and said first and second elastomeric gaskets is formed;

(D) means for maintaining the sealing array among the fluoride-sensing crystal, the first and second elastomeric gaskets, and the primary container body when they are jointly rotated, said means not including use of any cement or adhesive or any incorporation of the fluoride-sensing crystal into a cohesive unitary solid from which it can not be removed intact without dividing all parts of the unitary solid that do not consist of the fluoride-sensing crystal into at least two separate pieces;

(E) means for dividing the central cavity of the primary container body so as to constitute jointly with the primary container body, the fluoride-sensing crystal and at least one of the first and second elastomeric gaskets, boundaries of a liquid- and vapor-tight portion of the central cavity of the primary container body;

(F) a volume of a first liquid ionic solution of known composition and concentration confined within said substantially liquid- and vapor-tight portion of the central cavity of the primary container body and in physical contact with the fluoride-sensing crystal;

(G) a first reference electrode enclosed within said substantially liquid- and vapor-tight portion of the central cavity of the primary container body, said first reference electrode including a metallic electrical conductor that is in physical contact with the first liquid ionic solution but is not in physical contact with the fluoride-sensing crystal; and (H) an electrically conducted lead component that is in physical contact with both the metallic electrical conductor part of the first reference electrode and a point outside said substantially liquid- and vapor-tight portion of the central cavity of the primary container body but is not in physical contact with the fluoride-sensing crystal or with the first ionic solution, wherein: the central cavity of the primary container body has a central portion that is cylindrical; a first end portion of the central cavity of the primary container body has a shape of a cylinder that is concentric with but has a larger diameter than the cylindrical central portion of the central cavity, so that the primary container body in said first end portion has a bounding wall surface that consists of two concentric cylinders joined by an annular disk with a circular center hole, the disk and center hole both being concentric with said concentric cylinders; and a solid portion of said annular disc and an end portion of the walls of the primary container body surrounding the central cavity bound a space in which the sealing array of said fluoride-sensing crystal and said first and second elastomeric gaskets is retained.

2. A free-fluoride-ion-sensitive electrode according to claim 1, wherein the fluoride sensing crystal is a solid cylinder and each of the first and second elastomeric gaskets is a cylinder with a cylindrical hole therethrough or is a torus.

3. A free-fluoride-ion-sensitive electrode according to claim 2, wherein: the means for maintaining the sealing array of the fluoride-sensing crystal, the first and second elastomeric gaskets, and the primary container body comprises the following components:

(A') male screw threads on an exterior first end portion of the walls of the primary container body; and (B') a first end cap component comprising:
(1) a primary cylinder portion having a concentric cylindrical hole therethrough, so that the primary cylinder portion has exterior and interior walls and distinct first and second ends of each of the exterior and interior walls;
(2) a retainer portion joined to the primary cylinder portion at its second end; and
(3) a continuous zone of female screw threads on at least a part of the interior wall of the primary cylinder portion, said female screw threads being matable with the male screw threads on the exterior first end portion of the walls of the primary container body when these male screw threads are inserted into the first end of the interior walls of the first end cap component, said retainer portion and said primary cylinder portion together forming a liquid-tight container to retain the sealing array of said fluoride-sensing crystal and said first and second elastomeric gaskets, (i) said male screw threads on the primary container body, (ii) said first end cap component, (iii) said primary cylinder portion of the first end cap component, (iv) said concentric cylindrical hole therethrough, (v) said exterior and interior walls of the first end cap component, (vi) said female screw threads on at least a zone of said interior walls, (vii) said retainer portion of the first end cap component, and (viii) a hole therethrough all forming a torque-limited-screwed, temperature-stable sealing container around the sealing array of the fluoride-sensing crystal and the first and second elastomeric gaskets.

4. A free-fluoride-ion-sensitive electrode according to claim 3, wherein the means for dividing the central cavity of the primary container body is a plug of solidified potting resin through which electrically conducting lead component (H) passes.

5. A free-fluoride-ion-sensitive electrode according to claim 4, wherein: the central cavity through the primary container body has an enlarged zone which has two ends, both ends of said enlarged zone of the central cavity being within, rather than at either end of, the central cavity and both of the ends of the enlarged zone being between an end of the primary container body and the liquid- and vapor-tight portion of the central cavity that contains the first ionic solution of known composition, said enlarged zone being larger in cross-section than is another portion of said central cavity that is situated between the enlarged zone and one of said ends of said central cavity; and at least a portion of said plug of potting resin fits within said enlarged zone of the central cavity of the primary container body and has a larger cross-section than does a portion of said central cavity that is situated between the enlarged zone and said one of said ends of said central cavity.

6. A free-fluoride-ion-sensitive electrode according to claim 5, wherein a second end of the primary container body has a zone of male screw threads on its exterior surface and the second end of the central cavity through the primary container body is closed by a second end cap component comprising:
(1) a primary cylinder portion having a concentric cylindrical hole therethrough, so that the primary cylinder portion has exterior and interior walls and distinct first and second ends of each of the exterior and interior walls;
(2) a closure portion joined to the primary cylinder portion at the second end of its exterior and interior walls, said closure portion being a solid circular disk, except that electrical lead component (H) passes through it; and (3) a continuous zone of female screw threads on at least a part of the interior wall of the primary cylinder portion, said female screw threads being matable with the male screw threads on the exterior second end of the walls of the primary container body when these male screw threads are inserted into the first end of the interior walls of the second end cap component.

7. A free-fluoride-ion-sensitive electrode according to claim 6, wherein the primary container body and the end caps are constituted of polytetrafluoroethylene and the first and second elastomeric gaskets are constructed of a copolymer of tetrafluoroethylene and perfluoro(methylvinylether).

8. A free-fluoride-ion-sensitive electrode according to claim 3, wherein the primary container body and any end cap or caps present in the free-fluoride-ion-sensitive electrode have a modulus of elasticity in flexure from $1.0 \times 10^7$ to $5.0 \times 10^7$ kg/m$^2$ and the first and second elastomeric gaskets are constructed of a fluorocarbon elastomer.

9. A free-fluoride-ion-sensitive electrode according to claim 4, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

10. A free-fluoride-ion-sensitive electrode according to claim 5, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

11. A free-fluoride-ion-sensitive electrode according to claim 1, wherein: the means for maintaining the sealing array of the fluoride-sensing crystal, the first and second elastomeric gaskets, and the primary container body comprises the following components:

(A') male screw threads on an exterior first end portion of the walls of the primary container body; and (B') a first end cap component comprising:

(1) a primary cylinder portion having a concentric cylindrical hole therethrough, so that the primary cylinder portion has exterior and interior walls and distinct first and second ends of each of the exterior and interior walls;

(2) a retainer portion joined to the primary cylinder portion at its second end; and (3) a continuous zone of female screw threads on at least a part of the interior wall of the primary cylinder portion, said female screw threads being matable with the male screw threads on the exterior first end portion of the walls of the primary container body when these male screw threads are inserted into the first end of the interior walls of the first end cap component, said retainer portion and said primary cylinder portion together forming a liquid-tight container to retain the sealing array of said fluoride-sensing crystal and said first and second elastomeric gaskets, (i) said male screw threads on the primary container body, (ii) said first end cap component, (iii) said primary cylinder portion of the first end cap component, (iv) said concentric cylindrical hole therethrough, (v) said exterior and interior walls of the first end cap component, (vi) said female screw threads on at least a zone of said interior walls, (vii) said retainer portion of the first end cap component, and (viii) a hole therethrough all forming a torque-limited-screwed, temperature-stable sealed container around the sealing array of the fluoride-sensing crystal and the first and second elastomeric gaskets.

12. A free-fluoride-ion-sensitive electrode according to claim 11, wherein the means for dividing the central cavity of the primary container body is a plug of solidified potting resin through which electrically conducting lead component (H) passes.

13. A free-fluoride-ion-sensitive electrode according to claim 12, wherein: the central cavity through the primary container body has an enlarged zone which has two ends, both ends of said enlarged zone of the central cavity being within, rather than at either end of, the central cavity and both of the ends of the enlarged zone being between an end of the primary container body and the liquid- and vapor-tight portion of the central cavity that contains the first ionic solution of known composition, said enlarged zone being larger in cross-section than another portion of said central cavity that is situated between the enlarged zone and one of said ends of said central cavity; and at least a portion of said plug of potting resin fits within said enlarged zone of the central cavity of the primary container body and has a larger cross-section than does a portion of said central cavity that is situated between the enlarged zone and said one of said ends of said central cavity.

14. A free-fluoride-ion-sensitive electrode according to claim 13, wherein a second end of the primary container body has a zone of male screw threads on its exterior surface and the second end of the central cavity through the primary container body is closed by a second end cap component comprising:

(1) a primary cylinder portion having a concentric cylindrical hole therethrough, so that the primary cylinder portion has exterior and interior walls and distinct first and second ends of each of the exterior and interior walls;

(2) a closure portion joined to the primary cylinder portion at the second end of its exterior and interior walls, said closure portion being a solid circular disk, except that electrical lead component (H) passes through it; and (3) a continuous zone of female screw threads on at least a part of the interior wall of the primary cylinder portion, said female screw threads being matable with the male screw threads on the exterior second end of the walls of the primary container body when these male screw threads are inserted into the first end of the interior walls of the second end cap component.

15. A free-fluoride-ion-sensitive electrode according to claim 14, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

16. A free-fluoride-ion-sensitive electrode according to claim 11, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

17. A free-fluoride-ion-sensitive electrode according to claim 12, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

18. A free-fluoride-ion-sensitive electrode according to claim 13, wherein the primary container body and any end cap or caps present in the free-fluoride-ion-sensitive electrode are constituted of polytetrafluoroethylene and the first and second elastomeric gaskets are constructed of a copolymer of tetrafluoroethylene and perfluoro(methylvinylether).

\* \* \* \* \*

UNITED STATES PATENT AND TRADEMARK OFFICE
CERTIFICATE OF CORRECTION

PATENT NO. : 6,579,434 B1
DATED : June 17, 2003
INVENTOR(S) : Cornell et al.

It is certified that error appears in the above-identified patent and that said Letters Patent is hereby corrected as shown below:

Column 13,
Line 18, after "crystal" insert -- , --.
Line 35, delete "conducted" and insert -- conducting --.

Signed and Sealed this

Seventh Day of February, 2006

JON W. DUDAS
*Director of the United States Patent and Trademark Office*